United States Patent [19]

Lee

[11] 4,061,539

[45] Dec. 6, 1977

[54] PREPARATION AND USE OF GLUCOSE ISOMERASE

[75] Inventor: Chin Kee Lee, Winston-Salem, N.C.

[73] Assignee: R. J. Reynolds Tobacco Company, Winston-Salem, N.C.

[21] Appl. No.: 734,222

[22] Filed: Oct. 20, 1976

[51] Int. Cl.² .................................................. C12D 13/10
[52] U.S. Cl. ........................................ 195/31 F; 195/65
[58] Field of Search ..................... 195/65, 66 R, 31 F

[56] References Cited

U.S. PATENT DOCUMENTS

| 3,956,066 | 5/1976 | Coker et al. | 195/31 F |
| 3,979,261 | 9/1976 | Outtrup | 195/65 |

Primary Examiner—Lionel M. Shapiro
Attorney, Agent, or Firm—Manford R. Haxton; Herbert J. Bluhm

[57] ABSTRACT

Glucose is converted to fructose in the presence of an enzyme produced by *Flavobacterium arborescens*.

7 Claims, No Drawings

PREPARATION AND USE OF GLUCOSE ISOMERASE

SUMMARY OF INVENTION

Certain strains of *Flavobacterium arborescens* have been found to produce substantial amounts of glucose isomerase. This enzyme is very suitable for use in the isomerization of glucose to fructose.

BACKGROUND OF THE INVENTION

There has been considerable interest in recent years in the enzymatic conversion of glucose to fructose particularly in connection with the production of fructose-containing syrups from corn starch. The glucose isomerase used for this conversion can be obtained from microorganisms belonging to various genera including *Arthrobacter, Streptomyces, Bacillus* and *Actinoplanes.* Another source of glucose isomerase has recently been dislosed in U.S. Pat. No. 3,956,066 which issued on May 11, 1976. That patent describes the production of glucose isomerase by members of the species *Flavobacterium devorans.*

DETAILED DESCRIPTION

The present invention involves the discovery that certain strains of the species *Flavobacterium arborescens* are capable of producing glucose isomerase in significant quantities. This enzyme is eminently suited for use in a glucose isomerization process.

Although the organisms disclosed herein are identified as members of the species *Flavobacterium arborescens,* it should be noted that there is at present some controversy as to the proper classification of these organisms. Pages 362-363 of the 8th edition of Bergey's Manual of Determinative Bacteriology indicate that the species *F. arborescens* is improperly classified as a member of the genus *Flavobacterium.* A new classification and revised nomenclature have not yet been established for these organisms. Accordingly, the existing nomenclature will be used herein with the understanding that the *Flavobacterium* genus designation is not correct and that another genus designation will eventually be adopted in the reclassification of *Flavobacterium arborescens.* It should be also noted that *Flavobacterium devorans* referred to in U.S. Pat. No. 3,956,066 is not a candidate for reclassification and this fact represents one point of distinction between the present invention and the cited U.S. Patent.

The preferred organisms used in connection with the present invention are mutant strains isolated from culture ATCC 4358 which is available from the American Type Culture Collection. The preferred strains of *F. arborescens* capable of producing significant quantities of glucose isomerase have been deposited in the permanent ARS Culture Collection of the USDA Northern Regional Research Laboratory in Peoria, Ill. and are available as cultures NRRL B-11,022 and NRRL B-11,023.

The microorganisms disclosed herein may be cultivated in a variety of media containing sources of carbon, nitrogen and inorganic salts. A typical medium includes hydrolyzed animal protein, corn steep liquor, a brewer's yeast extract, potassium dihydrogen phosphate, potassium monohydrogen phosphate and a suitable carbohydrate. Carbohydrates which may be used include xylose, glucose, maltose, sucrose and lactose as well as hydrolysates of xylan, starch and cellulose. The initial pH of the growth medium is about 7 and the fermentation is conducted aerobically at approximately 30° C. in a suitable fermentor or shake flask. Maximum isomerase activity is generally attained in about 48 to 72 hours.

The isomerase activity produced by the microorganisms is assayed by incubating at 60° C. for 30 minutes a mixture containing 0.5 milliliter of the enzyme-containing preparation and 1.5 milliliters of a solution containing sufficient dextrose, Tricine buffer (pH 8) and magnesium chloride to give final concentrations of 1.0 M, 0.1 M and 0.03 M, respectively. At the end of the incubation period the isomerization reaction is terminated by the addition of 0.5 milliliter of 1.0 N hydrochloric acid. After centrifugation the clear supernatant fraction is properly diluted and the fructose produced is determined by the procedure of L. Messineo and E. Musarra as described in Int. J. Biochem. 3(18), 691–699 (1972). Isomerase activity is expressed in microunits with one microunit of activity defined as the quantity of enzyme that will produce one microgram of fructose per minute under the assay conditions described above.

The quantity of isomerase produced by the preferred strains under favorable cultivation conditions has been found to be quite substantial and significantly greater than with other isomerase-producing microorganisms disclosed in the prior art. Isomerase production by the preferred strains varies considerably depending on the cultivation conditions used. A particularly surprising and unexpected result is that maximum isomerase production has been found to occur when lactose is used in the growth medium. For example, cultivation of NRRL B-11,022 in a medium containing 2 percent lactose gave 2892 microunits of isomerase per milliliter of fermentation broth. Very substantial enzyme production also occurs when no carbohydrates are added to the medium. This is demonstrated by data shown in Table 1 based on cultivation at 30° C. of strains of *F. arborescens* in a medium containing 1% hydrolyzed animal protein (Bacto-Tryptone obtained from Difco Laboratories in Detroit, Michigan), 1% corn steep liquor, 1% yeast extract, 1% potassium momohydrogen phosphate, 0.5% potassium dihydrogen phosphate and 2% carbohydrate where indicated.

TABLE 1

| Isomerase Production by *F. arborescens* | | | |
|---|---|---|---|
| | | Isomerase Activity in Microunits/ml. | |
| Carbohydrate in Medium | Hours | ATCC 4358 | NRRL B-11,022 | NRRL B-11,023 |
| None | 72 | 0 | 1042 | 1480 |
| Xylose | 72 | 546 | 892 | 775 |
| Glucose | 72 | 0 | 89 | 1123 |
| Lactose | 72 | 0 | 2892 | 1679 |
| Maltose | 72 | — | 1314 | — |
| Sucrose | 72 | — | 1190 | — |

Isomerase produced by *F. arborescens* exhibits useful activity in the pH range of about 6 to 10 and a temperature of about 45° to 90° C. Table 2 shows the effect of pH and Table 3 shows the effect of temperature on isomerase activity associated with whole cells obtained by cultivating NRRL B-11,022 in a lactose-containing nutrient medium at 30° C. for 72 hours. Stablity of the enzyme is indicated by data in Table 4. For the data in Tables 2 and 3, harvested cells were washed once and resuspended in water to the original concentration of the cells in the fermentation broth. The standard assay procedure described above was used for measuring isomerase activity except that the buffer was varied in the pH study and the temperature was varied in the experiments on temperature effect. The stability study summarized in Table 4 involved incubation of washed cells in 0.05 M TRICINE buffer (pH 8) containing magnesium chloride (0.004 M) and assay of the incubated cells at the specified intervals using the standard assay procedure.

TABLE 2

Effect of pH on Isomerase from NRRL B-11,022

| Buffer | pH | Isomerase Activity in Microunits/ml. |
|---|---|---|
| PIPES[1] | 6.0 | 598 |
| PIPES[1] | 6.5 | 1204 |
| PIPES[1] | 7.0 | 1782 |
| PIPES[1] | 7.5 | 2202 |
| TRICINE[2] | 7.5 | 2624 |
| TRICINE[2] | 8.0 | 3016 |
| TRICINE[2] | 8.5 | 3456 |
| TRICINE[2] | 9.0 | 3408 |

[1]PIPES is monosodium 1,4-piperazinediethanesulfonic acid.
[2]TRICINE is N-[2-hydroxy-1,1-bis(hydroxymethyl)ethyl]glycine.

TABLE 3

Effect of Temperature on Isomerase from NRRL B-11,022 at pH 8.0

| Temperature in ° C. | Isomerase Activity in Microunits/ml. |
|---|---|
| 45 | 775 |
| 50 | 1717 |
| 55 | 2776 |
| 60 | 3500 |
| 65 | 4400 |
| 70 | 5104 |
| 75 | 5960 |
| 80 | 6592 |
| 85 | 7088 |

TABLE 4

Stability of Isomerase from NRRL B-11,022 at Selected Temperatures

| Total Incubation Time in Hours | Isomerase Activity in Microunits/ml. | |
|---|---|---|
| | 60° C. Incubation | 70° C. Incubation |
| 24 | 2212 | 2340 |
| 96 | 2276 | 2244 |
| 168 | 2276 | 2036 |
| 240 | 2262 | 2092 |

Isomerase produced by *F. arborescens* is very effective for converting glucose to fructose and various procedures already described in the prior art may be used for such conversions. For example, the whole cells may be used directly in a batch operation or the cells may be immobilized in a fixed bed for continuous operation. Alternatively, the isomerase may be liberated from the cells by known methods and used as soluble enzyme in a batch system or immobilized for use in a continuous process. Methods for using enzymes in such forms are well known as indicated, for example, in a review by W. R. Vieth and K. Venkatasubramanian published in CHEMTECH 3, 667–684 (1973) and 4, 47–55, 309–320 and 434–444 (1974).

Regardless of the form in which the isomerase is used for glucose isomerization, the reaction should be carried out at a temperature between 45° and 90° C. and preferably between about 60° and 75° C. The pH of the glucose-containing solution should be maintained between about 6 and 10 and preferably between about 6.5 and 8.0 in order to minimize formation of degradation products at the elevated temperatures. The enzyme is effective with relatively pure glucose solutions as well as with starch hydrolysates prepared by acid and/or enzyme treatment. Glucose concentrations of 30 to 60 percent by weight are preferred for the conversion step. Enzyme activity is enhanced by the addition of small quantities of magnesium ions to the glucose-containing solution. The fructose-containing solution obtained from the isomerization may be refined using conventional methods such as treatment with activated carbon and ion exchange resins.

The following examples will further illustrate the use and advantages of this invention.

EXAMPLE 1

In a 500-milliliter Erlenmeyer flask was placed 100 milliliters of nutrient medium containing the following:

| | Percent |
|---|---|
| Hydrolyzed animal protein | 1.0 |
| Corn steep liquor | 1.0 |
| Yeast extract | 1.0 |
| $K_2HPO_4$ | 1.0 |
| $KH_2PO_4$ | 0.5 |
| Lactose | 2.0 |

The above medium was inoculated with freshly prepared inoculum from *F. arborescens* NRRL B-11,022 and the inoculated medium was agitated at 30° C. using a rotary shaker. At the end of 72 hours the cells were harvested and washed. An assay revealed the presence of isomerase activity equivalent to 2892 microunits per milliliter of whole broth.

EXAMPLE 2

The isomerization of glucose to fructose was carried out by adding 10 grams of washed whole cells obtained by the procedure of Example 1 to 500 milliliters of a 50% (weight/volume) glucose syrup that was 0.01 M with respect to magnesium chloride. The pH of the syrup was adjusted to 8.0 by means of sodium hydroxide and the syrup was incubated at 60° C. with gentle stirring. After 20 hours the syrup was analyzed for fructose and it was found that 45% of the glucose had been converted to fructose.

EXAMPLE 3

The procedure of Example 1 was repeated except that xylose was used in the nutrient medium instead of lactose and the inoculum was prepared from *F. arborescens* ATCC 4358. After 72 hours the cells were harvested and an assay indicated the presence of isomerase activity equivalent to 546 microunits per milliliter of whole broth.

EXAMPLE 4

The procedure of Example 1 was repeated except that lactose was replaced by glucose in the nutrient medium and the inoculum was obtained from *F. arborescens* NRRL B-11,023. At the end of 64 hours the harvested cells were assayed and were found to have isomerase activity equivalent to 580 microunits per milliliter of whole broth.

EXAMPLE 5

Enzymatic conversion of glucose to fructose was effected by introducing 9 grams of wet cells obtained by the procedure of Example 4 into 500 milliliters of a 50% (weight/volume) glucose solution that was 0.005 M with respect to magnesium chloride. The pH of the syrup was adjusted to 8.0 by means of sodium hydroxide and the solution was incubated at 60° C. with gentle stirring. Analysis of the solution after 27 hours revealed a fructose content of 38%.

EXAMPLE 6

F. arborescens NRRL B-11,022 was cultivated at 30° C. for 70 hours in a 10-liter New Brunswick fermentor using the nutrient medium described in Example 1. The cells were harvested and immobilized by the flocculation procedure disclosed in U.S. Pat. No. 3,821,086 to give a dried, flocculated cell aggregate exhibiting 75 microunits per gram isomerase activity. A 1-inch diameter glass column containing 5 grams of the dried aggregate was used for continuous glucose isomerization. The column was maintained at 60° C. and a 50% (weight/volume) glucose solution that was 0.005 M with respect to magnesium chloride and adjusted to pH 8.0–8.4 was passed through the column at a flow rate of 26 milliliters per hour. Effluent from the column was analyzed for fructose and the degree of conversion of glucose to fructose was found to be approximately 45%.

What is claimed is:

1. A process for preparing a glucose-isomerizing enzyme which comprises cultivating a microorganism belonging to the species *Flavobacterium arborescens* in a nutrient medium under conditions suitable for production of said enzyme by said microorganism and recovering said enzyme.

2. A process according to claim 1 in which the microorganism is *Flavobacterium arborescens* ATCC 4358.

3. A process according to claim 1 in which the microorganism is *Flavobacterium arborescens* NRRL B-11,022.

4. A process according to claim 1 in which the microorganism is *Flavobacterium arborescens* NRRL B-11,023.

5. A process for converting glucose to fructose which comprises contacting a glucose-containing solution with a glucose-isomerizing enzyme derived from a microorganism belonging to the species *Flavobacterium arborescens* and recovering a fructose-containing liquor.

6. A process according to claim 5 wherein said process is carried out at a temperature of about 45° C. to about 90° C. in a pH range of approximately 6 to 10.

7. A process according to claim 5 wherein said microorganism is selected from the group consisting of *F. arborescens* ATCC 4358, NRRL B-11,022 and NRRL B-11,023.

* * * * *